(12) United States Patent
Ma et al.

(10) Patent No.: US 8,748,669 B2
(45) Date of Patent: Jun. 10, 2014

(54) PROCESS FOR PRODUCING ALDEHYDES OR KETONES BY OXIDIZING ALCOHOLS WITH OXYGEN

(75) Inventors: Shengming Ma, Shanghai (CN); Jinxian Liu, Shanghai (CN); Jinqiang Kuang, Shanghai (CN); Yu Liu, Shanghai (CN); Yuli Wang, Shanghai (CN); Qiong Yu, Shanghai (CN); Weiming Yuan, Shanghai (CN); Suhua Li, Shanghai (CN); Bo Chen, Shanghai (CN); Jiajia Cheng, Shanghai (CN); Baoqiang Wan, Shanghai (CN); Juntao Ye, Shanghai (CN); Shichao Yu, Shanghai (CN)

(73) Assignees: East China Normal University, Shanghai (CN); Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 141 days.

(21) Appl. No.: 13/497,960

(22) PCT Filed: Jul. 30, 2010

(86) PCT No.: PCT/CN2010/075608
§ 371 (c)(1), (2), (4) Date: Mar. 23, 2012

(87) PCT Pub. No.: WO2012/012952
PCT Pub. Date: Feb. 2, 2012

(65) Prior Publication Data
US 2012/0220792 A1     Aug. 30, 2012

(30) Foreign Application Priority Data
Jul. 26, 2010   (CN) ............................ 2010 1 0237170

(51) Int. Cl.
*C07C 45/38*   (2006.01)
*C07C 45/39*   (2006.01)

(52) U.S. Cl.
USPC ............................ 568/320; 568/391; 568/472

(58) Field of Classification Search
CPC .... B01J 31/006; B01J 31/28; B01J 2231/763; B01J 2561/842; C07C 45/38; C07C 45/39; C07C 47/232; C07C 49/235
USPC .......................................... 568/320, 391, 472
See application file for complete search history.

(56) References Cited

U.S. PATENT DOCUMENTS

2007/0078284 A1    4/2007   Tanielyan et al.

FOREIGN PATENT DOCUMENTS

| CN | 101544548 A | 9/2009 |
| CN | 101565344 A | 10/2009 |

OTHER PUBLICATIONS

International Search Report for PCT/CN2010/075608 dated Apr. 28, 2011.

*Primary Examiner* — Sikarl Witherspoon
(74) *Attorney, Agent, or Firm* — Birch, Stewart, Kolasch & Birch, LLP

(57) ABSTRACT

Provided is a process for producing aldehydes or ketones by oxidizing alcohols with oxygen, which comprises oxidizing alcohols to aldehydes or ketones in an organic solvent at room temperature with oxygen or air as an oxidant, wherein ferric nitrate (Fe(NO3)3.9H2O), 2,2,6,6-tetramethylpiperidine N-oxyl (TEMPO) and an inorganic chloride are used as catalysts, the reaction time is 1-24 hours, and the molar ratio of said alcohols, 2,2,6,6-tetramethylpiperidine N-oxyl and the inorganic chloride is 100:1~10:1~10:1~10. The present process has the advantages of high yield, mild reaction conditions, simple operation, convenient separation and purification, recoverable solvents, substrates used therefor being various and no pollution, and therefore it is adaptable to industrialization.

6 Claims, No Drawings

PROCESS FOR PRODUCING ALDEHYDES OR KETONES BY OXIDIZING ALCOHOLS WITH OXYGEN

FIELD OF THE TECHNOLOGY

The present invention relates to a process for producing aldehydes or ketones by aerobic oxidation of alcohols with a ferrous catalyst.

BACKGROUND OF THE TECHNOLOGY

Aldehydes and ketones are known as important raw materials in fine chemical industry, and are widely applied in industrial chemical production as well as in academic research laboratories. Oxidation is a type of basic and crucial chemical transformation. In industry, aldehydes and ketones are prepared mainly by oxidation. Hence it is promising to develop an economic, mild, eco-friendly and efficient catalytic oxidation method. Traditionally, aldehydes and ketones are prepared by oxidation of corresponding alcohols using at least stoichiometric amount of oxidants. Although this protocol enables the preparation of aldehydes and ketones, however, the use of oxidant such as chromium oxide, manganese oxide and ruthenium oxide etc., would yield almost the same amount of oxidant-derived waste, which causes a serious burden to the environment. Therefore such method is not suitable for large-scale industrial production (*Chromium Oxidations in Organic Chemistry*; Springer: Berlin, 1984; Regen, S. L.; Koteel, C. J. Am. Chem. Soc. 1977, 99, 3837-3838; Griffith, W. P. Chem. Soc. Rev. 1992, 21, 179-185). Thus much attention has been paid to methods for preparing aldehydes and ketones by catalytic oxidation of corresponding primary or secondary alcohols using oxygen as oxidant with transition metals such as Pd, Ru, Mo—Co, Co, Pt, Os—Cu, Os, Ni, Cu, Fe etc. (Blackburn, T. F.; Schwartz, J. *J. Chem. Soc. Chem. Commun.* 1977, 157-158; Piera, J.; Backvall, J.-E. Angew. Chem. Int. Ed. 2008, 47, 3506; Sheldon, R. A.; Arends, I. W. C. E.; Brink, G.-J. T.; Dijksman, A. *Acc. Chem. Res.* 2002, 35, 774; Mallat, T.; Baiker, A. Chem. Rev. 2004, 104, 3037). TEMPO, as a stable oxygen free radical, plays an important role in synergetic catalytic oxidation with Fe or Cu of primary or secondary alcohols to prepare the corresponding aldehydes or ketones.

The present invention overcomes a series of defects of existing technologies such as the use of heavy metals as catalyst, rigorous reaction conditions, time-consuming, limited scope of substrates, high reaction temperature and reaction pressure etc., and thereby provides an efficient method for preparing aldehydes or ketones by aerobic oxidation under atmospheric pressure. In said method, ferric nitrate, TEMPO, and inorganic chlorides are used as co-catalyst, oxygen is used as oxidant, and thereby brings advantages including the reducing chemical wastes, pollutions, cost, and various resources for starting materials, as well as mild reaction conditions and high efficiency. The method according to the present invention is suitable for large-scale industrial production and is eco-friendly.

SUMMARY OF INVENTION

The present invention provides a method for preparing aldehydes and ketones by a catalytic aerobic oxidation of alcohols under mild reaction conditions and meanwhile possesses such advantages as high efficiency, low cost and being eco-friendly.

The method for preparing aldehydes or ketones by aerobic oxidation of alcohols according to the present invention comprises a step of oxidizing alcohol to aldehyde or ketone at room temperature in an organic solvent for about 1 to about 24 hours using oxygen or air as oxidant, and using ferric nitrate, 2.2.6.6-tetramethylpiperidinyloxy(TEMPO) and inorganic chlorides as catalysts, wherein a molar ratio of said alcohol to said 2.2.6.6-tetramethylpiperidinyloxy, to said ferric nitrate, and to said inorganic chlorides is about 100:1~10:1~10:1~10.

Suitable alcohols according to the present invention include $R_1R_2CHOH$ and C5-C8 cyclic alcohols. In said molecular formula of $R_1R_2CHOH$, $R_1$ represents hydrogen; C1-16 alkyl; an alkenyl substituted with groups $R_3$ and/or $R_4$; allenyl substituted with groups $R_5$ and/or $R_6$; alkynyl substituted with group $R_7$, aryl, trifluoromethylphenyl, nitrophenyl, halophenyl or C1-C4 alkoxyphenyl; and $R_2$ represents hydrogen, C1-16 alkyl, aryl, trifluoromethylphenyl, halophenyl or methoxyphenyl, in which $R_3$ represents C1-C6 alkyl or aryl; $R_4$ represents hydrogen, C1-C6 alkyl or aryl; $R_5$ represents hydrogen, C1-C9 alkyl, arylphenyl or benzyl; $R_6$ represents hydrogen, C4-C9 alkyl, aryl or benzyl; and R7 represents hydrogen, C1-C12 alkyl, trimethylsilyl, aryl, halophenyl, nitrophenyl or methoxyphenyl. The said aryl is phenyl, halophenyl, alkoxyphenyl or naphthyl.

The C5-C8 cyclic alcohols according to the present invention is cyclopentanol, cyclohexanol, cycloheptanol or cyclooctanol.

Suitable organic solvents according to the present invention include benzene, toluene, dichloromethane, 1,2-dichloroethane, 1,1-dichloroethane, 1,2-dichloropropane, 1,3-dichloropropane, nitromethane, ethylene glycol dimethyl ether, tetrahydrofuran, acetonitrile or ethyl acetate or any combinations thereof.

Suitable inorganic chlorides according to the present invention include sodium chloride, potassium chloride, lithium chloride, rubidium chloride or cesium chloride, and preferably is sodium chloride.

The molar ratio of said alcohol to said 2.2.6.6-tetramethylpiperidinyloxy, to said ferric nitrate, and to said inorganic chlorides according to the present invention is preferably about 100:5:10:10.

The present invention discloses a method for preparing aldehydes or ketones by oxidation of alcohols in an organic solvent at room temperature using oxygen as oxidant and $Fe(NO_3)_3.9H_2O$, TEMPO (2,2,6,6-tetramethylpiperidinyloxy) and inorganic chloride (NaCl) as catalysts. The method of the present invention selectively oxidizes an alcohol with functional groups such as carbon-carbon single bond, carbon-carbon double bond or a carbon-carbon triple bond etc. with oxygen in the air or pure oxygen under atmospheric pressure and produces corresponding aldehyde and ketone of a primary alcohol or a secondary alcohol by oxidation. The advantages of the method according to the present invention include high yield, mild reaction conditions, simple operation, convenient separation and purification of products, recyclable solvents, various resources for starting materials, being eco-friendly, and no pollution etc. The present invention is suitable for application in industrial production.

One advantage of the present invention is that the substrates are available from various resources. The present invention uses $Fe(NO_3)_3.9H_2O$, TEMPO and inorganic chloride as co-catalyst, which can catalytic oxidize not only normal alcohols, benzylic alcohols, enols, cyclic alcohols etc., but also alcohols bearing much complicated structure such as propargylic alcohol and allenol etc. The method according to the present invention has advantages of mild reaction conditions, simple operations, convenient separation and purification of products, and the solvents being recoverable. Besides, the method according to the present invention has high yield and catalyst efficiency. For instance, an effective reaction can be initiated even if the content of catalysts is as low as 1 mol %. The method of the present invention overcomes a series of defects of existing technologies such as use of heavy metals as catalyst, rigorous reaction conditions, the reaction as being time-consuming, and limited catalyst substrates. The method of the present invention is not only suitable for small-scale synthesis in laboratories, but also for large scale industrial production.

The method according to the present invention uses oxygen or air, which is low-cost, and abundant in amount, replacing the chemical oxidants in conventional oxidation systems. The reaction can be conducted at room temperature under atmospheric pressure and neutral conditions, and the operations are convenient and controllable. For example, the reaction goes on well at room temperature under atmospheric pressure. Because of the use of oxygen as oxidant in the process according to the present invention, byproduct of the reaction is water, which will not result in any pollution to the environment, if treated properly, thus it is a green chemosynthesis. The present invention with simple working and high yield, effectively lowers the cost of production.

EMBODIMENTS OF THE INVENTION

Detailed description will be described now for better understating of the present invention, but not for limiting the contents of the present invention.

Example 1

Preparation of 2-benzylbuta-2,3-dienal

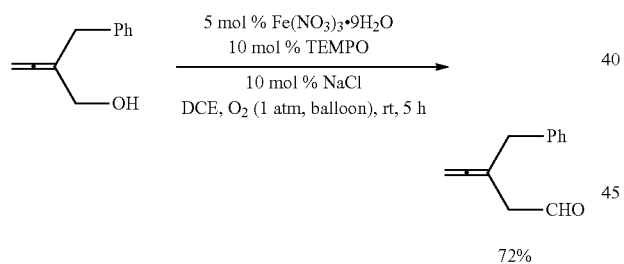

72% wherein, atm stands for atmospheric pressure, rt stands for room temperature.

$Fe(NO_3)_3 \cdot 9H_2O$ (20.3 mg, 0.05 mmol), 1,2-dichloroethane (DCE, 4 mL), 2,2,6,6-tetramethylpiperidinyloxy (TEMPO, 15.6 mg, 0.10 mmol) and NaCl (5.8 mg, 0.10 mmol) were added to a 10 mL-three-necked flask and were stirred for 5 mins at room temperature under oxygen atmosphere. 2-benzylbuta-2,3-dienol (160.6 mg, 1.0 mmol) was dissolved in DCE (1 mL) and then added to the reaction solution dropwise, and the reaction was monitored by TLC till it was complete. Then the reaction solution was diluted with ether (30 mL), dried over anhydrous $MgSO_4$, filtered by a short pad of silica gel, and then concentrated to yield the crude products. Further purification by column chromatography on silica gel (petroleum ether:ethyl acetate=20:1) afforded the target product 2-benzylbuta-2,3-dienal (114.5 mg, 72%). $^1H$ NMR (300 MHz, $CDCl_3$) δ 9.61 (s, 1H), 7.31-7.15 (m, 5H), 5.28 (t, J=2.4 Hz, 2H), 3.52 (t, J=2.6 Hz, 2H); $^{13}C$ NMR (75.4 MHz, $CDCl_3$) δ 222.50, 191.41, 138.52, 128.84, 128.35, 126.41, 110.62, 80.83, 30.84; IR (neat) 2827, 2728, 1955, 1928, 1677, 1602, 1495, 1454, 1426, 1227, 1144, 1071, 1030 $cm^{-1}$; MS (EI) m/z 158 ($M^+$, 5.25), 129 (100); HRMS: calcd. for $C_{11}H_{10}O$ ($M^+$): 158.0732. found: 158.07333.

Example 2

Preparation of 2,3-tridecadienal

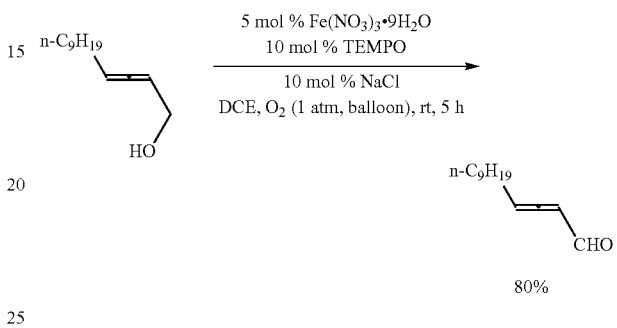

80%

Example 2 was conducted in the same manner as example 1 except that the raw material was 2,3-tridecadienol and the reaction continues for 5 hours. The resulting product was 2,3-tridecadienal, and the yield was 80%. $^1H$ NMR (300 MHz, $CDCl_3$) δ 9.44 (d, J=7.2 Hz, 1H), 5.84-5.71 (m, 2H), 2.25-2.10 (m, 2H), 1.55-1.42 (m, 2H), 1.42-1.20 (m, 12H), 0.84 (t, J=6.6 Hz, 3H); $^{13}C$ NMR (75.4 MHz, $CDCl_3$) δ 218.94, 192.00, 98.47, 96.19, 31.73, 29.38, 29.17, 29.15, 28.82, 28.71, 27.36, 22.53, 13.94; MS (EI) m/z 194 ($M^+$, 0.79), 81 (100); IR (neat) 2924, 2854, 1943, 1690, 1465, 1107, 1081 $cm^{-1}$; HRMS: calcd. for $C_{13}H_{22}O$ ($M^+$): 194.1671. found: 194.1671.

Example 3

Preparation of trideca-1,2-dien-4-one

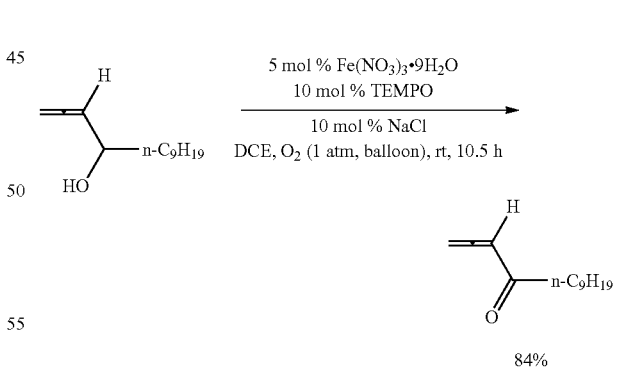

84%

Example 3 was conducted in the same manner as example 1 except that the raw material was trideca-1,2-dien-4-ol (196.2 mg, 1.0 mmol) and the reaction continues for 10.5 hours. The resulting product was trideca-1,2-dien-4-one (161.7 mg, 84%). $^1H$ NMR (300 MHz, $CDCl_3$) δ 5.74 (t, J=6.5 Hz, 1H), 5.20 (d, J=6.3 Hz, 2H), 2.57 (t, J=7.4 Hz, 2H), 1.63-1.50 (m, 2H), 1.35-1.17 (m, 12H), 0.85 (t, J=6.3 Hz, 3H); $^{13}C$ NMR (75.4 MHz, $CDCl_3$) δ 216.57, 200.88, 96.62, 79.16, 39.19, 31.81, 29.37, 29.33, 29.19, 29.14, 24.53, 22.59,

Example 4

Preparation of 2-hexyl-1-phenylbuta-2,3-dien-1-one

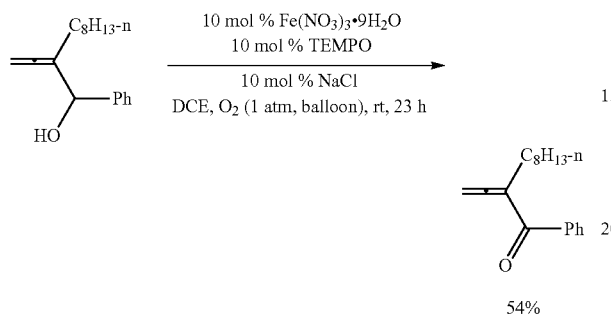

54%

Example 4 was conducted in the same manner as example 1 except that the raw material was 2-hexyl-1-phenylbuta-2,3-dien-1-ol (229.4 mg, 1.0 mmol) and the reaction continues for 23 hours. The resulting product was 2-hexyl-1-phenylbuta-2,3-dien-1-one (123.1 mg, 54%). $^1$H NMR (300 MHz, CDCl$_3$) δ 7.76 (d, J=7.8 Hz, 2H), 7.49 (t, J=7.1 Hz, 1H), 7.38 (t, J=7.7 Hz, 2H), 5.04 (t, J=2.7 Hz, 2H), 2.45-2.35 (m, 2H), 1.58-1.25 (m, 8H), 0.90 (t, J=6.5 Hz, 3H); $^{13}$C NMR (75.4 MHz, CDCl$_3$) δ 216.95, 194.78, 138.34, 131.85, 128.97, 127.73, 106.88, 79.26, 31.56, 28.85, 27.83, 27.80, 22.53, 13.98; IR (neat) 3059, 2955, 2856, 1932, 1650, 1598, 1579, 1447, 1315, 1269, 1177, 1072 cm$^{-1}$; MS (EI) m/z 228 (M$^+$, 1.69), 105 (100); HRMS: calcd. for C$_{16}$H$_{20}$O (M$^+$): 228.1514. found: 228.1512.

Example 5

Preparation of 1-(4-chlorophenyl)buta-2,3-dien-1-one

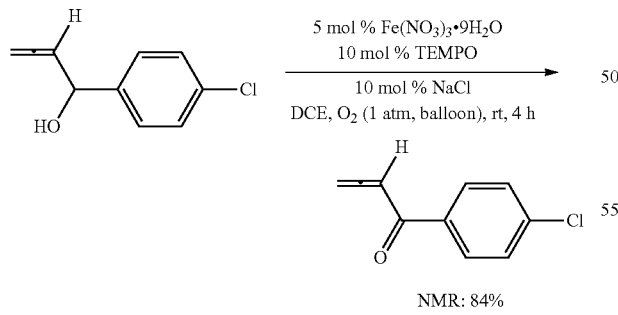

NMR: 84%

Example 5 was conducted in the same manner as example 1 except that the raw material was 1-(4-chlorophenyl)buta-2,3-dien-1-ol (180.1 mg, 1.0 mmol) and the reaction continues for 4 hours. The resulting product was 1-(4-chlorophenyl)buta-2,3-dien-1-one (unstable upon evaporation, NMR yield 84%). $^1$H NMR (300 MHz, CDCl$_3$) δ 7.83 (d, J=8.1 Hz, 2H), 7.41 (d, J=7.8 Hz, 2H), 6.38 (t, J=6.5 Hz, 1H), 5.26 (d, J=6.3 Hz, 2H); $^{13}$C NMR (75.4 MHz, CDCl$_3$) δ 216.38, 188.88, 138.41, 134.99, 129.38, 127.95, 92.46, 78.76; IR (neat): 1961, 1931, 1652, 1588, 1277, 1212, 1091 cm$^{-1}$; MS (EI) m/z 180 (M($^{37}$Cl)$^+$, 2.53), 178 (M($^{35}$Cl)$^+$, 10.29), 139 (100); HRMS: calcd. for C$_{10}$H$_7^{35}$ClO (M$^+$): 178.0185. found: 178.0185.

Example 6

Preparation of 3-hexylocta-1,2-dien-4-one

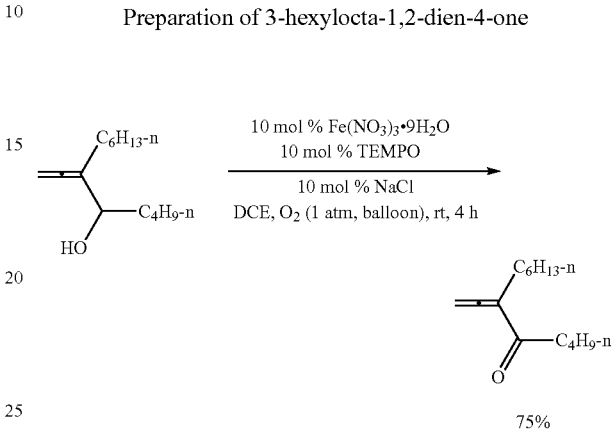

75%

Example 6 was conducted in the same manner as example 1 except that the raw material was 3-hexylocta-1,2-dien-4-ol (211.3 mg, 1.0 mmol) and the reaction continues for 4 hours. The resulting product was 3-hexylocta-1,2-dien-4-one (156.1 mg, 75%). $^1$H NMR (300 MHz, CDCl$_3$) δ 5.16 (t, J=2.9 Hz, 2H), 2.64 (t, J=7.7 Hz, 2H), 2.20-2.10 (m, 2H), 1.61-1.49 (m, 2H), 1.42-1.21 (m, 10H), 0.93-0.82 (m, 6H); $^{13}$C NMR (75.4 MHz, CDCl$_3$) δ 216.25, 201.38, 108.62, 79.35, 38.94, 31.61, 28.88, 27.82, 27.21, 26.27, 22.58, 22.37, 14.02, 13.82; IR (neat): 2957, 2928, 2858, 1934, 1677, 1464, 1410, 1379, 1349, 1259, 1175, 1086, 1020 cm$^{-1}$; MS (EI) m/z 208 (M$^+$, 0.48), 85 (100); HRMS: calcd. for C$_{14}$H$_{24}$O (M$^+$): 208.1827. found: 208.1826.

Example 7

Preparation of non-2-ynal

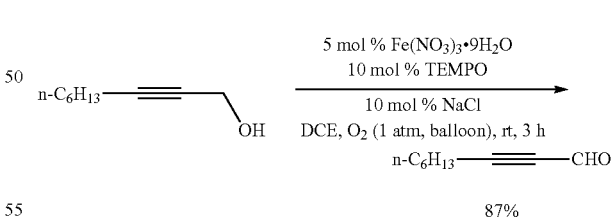

87%

Example 7 was conducted in the same manner as example 1 except that the raw material was non-2-ynol (140.1 mg, 1.0 mmol) and the reaction continues for 3 hours. The resulting product was non-2-ynal (119.9 mg, 87%). $^1$H NMR (300 MHz, CDCl$_3$) δ 9.18 (s, 1H), 2.41 (t, J=7.1 Hz, 2H), 1.66-1.50 (m, 2H), 1.48-1.24 (m, 6H), 0.90 (t, J=6.6 Hz, 3H); $^{13}$C NMR (75.4 MHz, CDCl$_3$) δ 176.86, 99.20, 81.61, 31.07, 28.39, 27.41, 22.34, 19.00, 13.86; IR (neat) 2930, 2859, 2237, 2200, 1716, 1670, 1458, 1380, 1278, 1225, 1137 cm$^{-1}$; MS (EI) m/z 138 (M$^+$, 0.40), 137 (M$^+$-H, 1.57), 41 (100).

Example 8

Preparation of 3-phenylpropynal

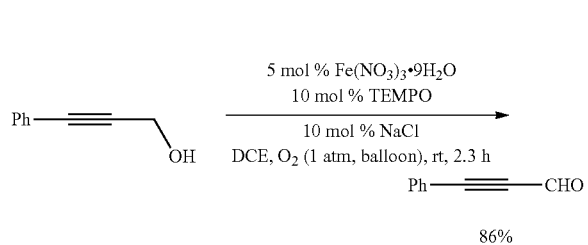

Example 8 was conducted in the same manner as example 1 except that the raw material was 3-phenylpropynol (132.0 mg, 1.0 mmol) and the reaction continues for 2.3 hours. The resulting product was 3-phenylpropynal (111.9 mg, 86%). $^1$H NMR (300 MHz, CDCl$_3$) δ 9.41 (s, 1H), 7.59 (d, J=7.8 Hz, 2H), 7.48 (t, J=6.9 Hz, 1H), 7.39 (t, J=6.9 Hz, 2H); $^{13}$C NMR (75.4 MHz, CDCl$_3$) δ 176.61, 133.16, 131.19, 128.65, 119.34, 94.96, 88.35; IR (neat) 2854, 2738, 2240, 2185, 1654, 1489, 1443, 1387, 1260, 1070 cm$^{-1}$; MS (EI) m/z 130 (M$^+$, 64.02), 102 (100).

Example 9

Preparation of 3-(4-nitrophenyl)propynal

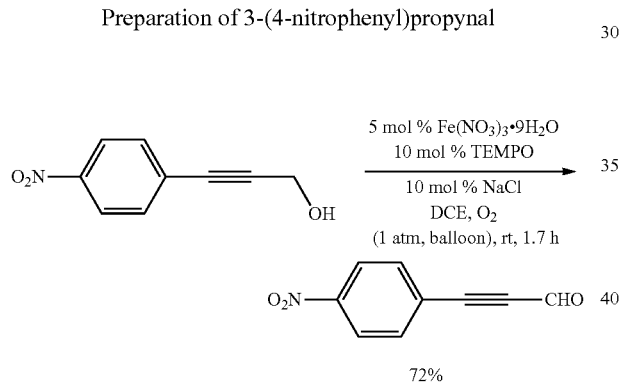

Example 9 was conducted in the same manner as example 1 except that the raw material was 3-(4-nitrophenyl)prop-2-yn-1-ol (177.5 mg, 1.0 mmol) and the reaction continues for 1.7 hours. The resulting product was 3-(4-nitrophenyl)propynal (125.5 mg, 72%). $^1$H NMR (300 MHz, CDCl$_3$) δ 9.43 (s, 1H), 8.24 (d, J=8.4 Hz, 2H), 7.75 (d, J=8.7 Hz, 2H); $^{13}$C NMR (75.4 MHz, CDCl$_3$) δ 176.03, 148.70, 133.78, 125.87, 123.71, 90.67, 90.49; IR (neat) 2924, 2854, 2195, 1655, 1592, 1511, 1342, 1103 cm$^{-1}$.

Example 10

Preparation of 3-(4-methoxyphenyl)propynal

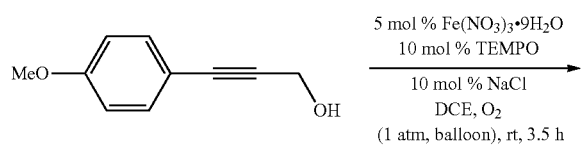

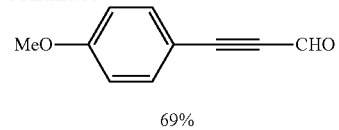

Example 10 was conducted in the same manner as example 1 except that the raw material was 3-(4-methoxyphenyl)prop-2-yn-1-ol (161.9 mg, 1.0 mmol) and the reaction continues for 3.5 hours. The resulting product was 3-(4-methoxyphenyl)propynal (110.8 mg, 69%). $^1$H NMR (300 MHz, CDCl$_3$) δ 9.38 (s, 1H), 7.54 (d, J=8.7 Hz, 2H), 6.90 (d, J=8.7 Hz, 2H), 3.83 (s, 3H); $^{13}$C NMR (75.4 MHz, CDCl$_3$) δ 176.32, 161.78, 135.03, 114.14, 110.67, 96.15, 88.37, 55.07; IR (neat) 2178, 1643, 1598, 1507, 1303, 1254, 1175, 1022 cm$^{-1}$; MS (EI) m/z (%) 160 (M$^+$, 100).

Example 11

Preparation of 1-(4-trifluoromethylphenyl)hept-2-yn-1-one

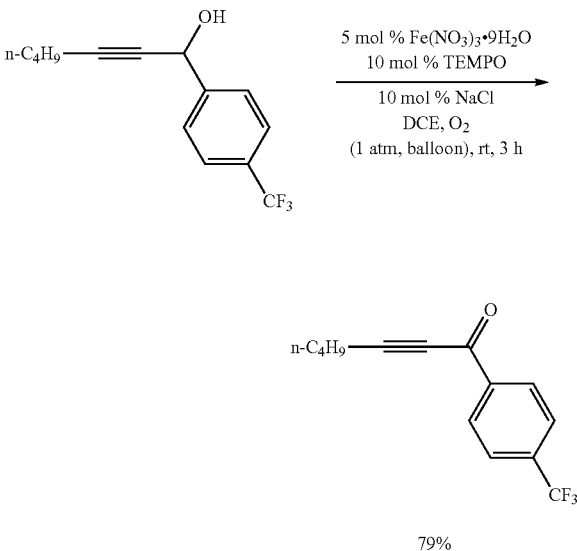

Example 11 was conducted in the same manner as example 1 except that the raw material was 1-(4-trifluoromethylphenyl)hept-2-yn-1-ol (256.3 mg, 1.0 mmol) and the reaction continues for 3 hours. The resulting product was 1-(4-trifluoromethylphenyl)hept-2-yn-1-one (201.0 mg, 79%). $^1$H NMR (300 MHz, CDCl$_3$) δ 8.24 (d, J=8.1 Hz, 2H), 7.74 (d, J=8.1 Hz, 2H), 2.54 (t, J=6.9 Hz, 2H), 1.75-1.61 (m, 2H), 1.58-1.44 (m, 2H), 0.98 (t, J=7.4 Hz, 3H); $^{13}$C NMR (75.4 MHz, CDCl$_3$) δ 176.78, 139.45, 134.91 (q, J=32.3 Hz), 129.70, 125.60-125.40 (m), 123.54 (q, J=272.6 Hz), 98.27, 79.38, 29.70, 22.02, 18.85, 13.37; IR (neat) 2962, 2936, 2875, 2239, 2201, 1650, 1583, 1509, 1466, 1411, 1322, 1261, 1170, 1128, 1108, 1064, 1016 cm$^{-1}$; MS (EI) m/z 254 (M$^+$, 3.14), 173 (100); HRMS: calcd. for $C_{14}H_{13}OF_3$ (M$^+$): 254.0918. found: 254.0919.

Example 12

Preparation of 1-phenylhept-1-yn-3-one

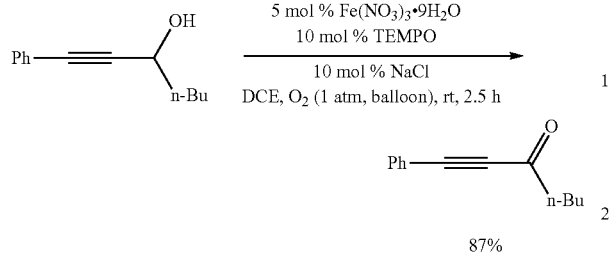

87%

Example 12 was conducted in the same manner as example 1 except that the raw material was 1-phenylhept-1-yn-3-ol (187.8 mg, 1.0 mmol) and the reaction continues for 2.5 hours. The resulting product was 1-phenylhept-1-yn-3-one (161.3 mg, 87%). $^1$H NMR (300 MHz, CDCl$_3$) δ 7.56 (d, J=7.5 Hz, 2H), 7.47-7.30 (m, 3H), 2.66 (t, J=7.4 Hz, 2H), 1.78-1.64 (m, 2H), 1.46-1.31 (m, 2H), 0.95 (t, J=7.4 Hz, 3H); $^{13}$C NMR (75.4 MHz, CDCl$_3$) δ 188.01, 132.87, 130.50, 128.50, 119.97, 90.37, 87.77, 45.14, 26.14, 22.05, 13.70; IR (neat) 3063, 2958, 2872, 2201, 1666, 1489, 1443, 1272, 1158, 1125, 1067 cm$^{-1}$; MS (EI) m/z 186 (M$^+$, 1.67), 129 (100).

Example 13

Preparation of 1-(tert-butyldimethylsilyloxy)undec-2-yn-4-one

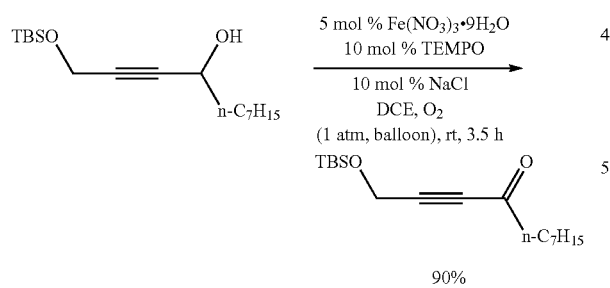

90%

Example 13 was conducted in the same manner as example 1 except that the raw material was 1-(tert-butyldimethylsilyloxy)undec-2-yn-4-ol (21-97.5 mg, 1.0 mmol) and the reaction continues for 3.5 hours. The resulting product was 1-(tert-butyldimethylsilyloxy)undec-2-yn-4-one (267.1 mg, 90%). $^1$H NMR (300 MHz, CDCl$_3$) δ 4.46 (s, 2H), 2.54 (t, J=7.4 Hz, 2H), 1.74-1.62 (m, 2H), 1.38-1.22 (m, 8H), 0.96-0.86 (m, 12H), 0.13 (s, 6H); $^{13}$C NMR (75.4 MHz, CDCl$_3$) δ 187.71, 90.19, 83.88, 51.50, 45.33, 31.59, 28.95, 28.90, 25.70, 23.97, 22.55, 18.22, 14.0, −5.23; IR (neat) 2929, 2857, 2216, 1679, 1464, 1364, 1255, 1153, 1098 cm$^{-1}$; MS (EI) m/z 296 (M$^+$, 0.15), 239 (M$^+$-Bu$^t$, 67.49), 75 (100); HRMS: calcd. for $C_{17}H_{32}O_2Si$ (M$^+$): 296.2172. found: 296.2174.

Example 14

Preparation of 1-phenyl-3-(trimethylsilyl)propynone

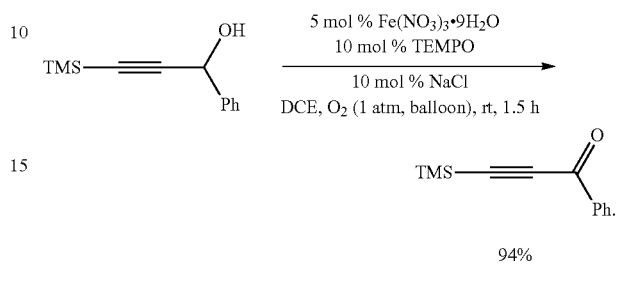

94%

Example 14 was conducted in the same manner as example 1 except that the raw material was 1-phenyl-3-(trimethylsilyl) propynol (204.9 mg, 1.0 mmol) and the reaction continues for 1.5 hours. The resulting product was 1-phenyl-3-(trimethylsilyl)propynone (191.0 mg, 94%). $^1$H NMR (300 MHz, CDCl$_3$) δ 8.14 (d, J=8.1 Hz, 2H), 7.61 (t, J=7.4 Hz, 1H), 7.48 (t, J=7.7 Hz, 2 H), 0.32 (s, 9H); $^{13}$C NMR (75.4 MHz, CDCl$_3$) δ 177.64, 136.48, 134.11, 129.60, 128.54, 100.84, 100.49, −0.73; IR (neat) 2153, 1643, 1598, 1579, 1450, 1312, 1243, 1173, 1035, 1016 cm$^{-1}$; MS (EI) m/z 202 (M$^+$, 16.37), 187 (100).

Example 15

Preparation of 1-(4-methoxyphenyl)hept-2-yn-1-one

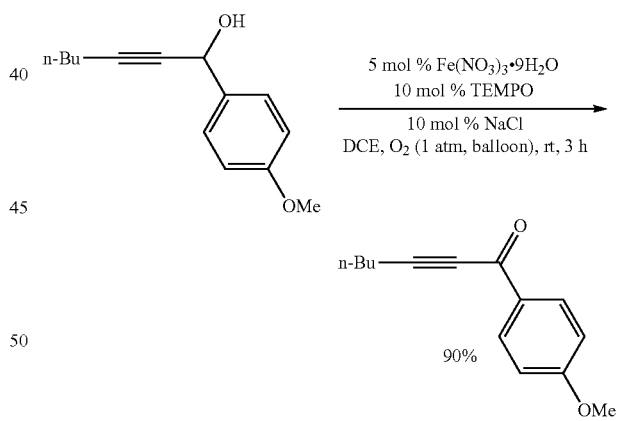

90%

Example 15 was conducted in the same manner as example 1 except that the raw material was 1-(4-methoxyphenyl)hept-2-yn-1-ol (218.7 mg, 1.0 mmol) and the reaction continues for 3 hours. The resulting product was 1-(4-methoxyphenyl) hept-2-yn-1-one (195.0 mg, 90%). $^1$H NMR (300 MHz, CDCl$_3$) δ 8.10 (d, J=8.4 Hz, 2H), 6.94 (d, J=8.7 Hz, 2H), 3.87 (s, 3H), 2.48 (t, J=6.9 Hz, 2H), 1.71-1.58 (m, 2H), 1.57-1.42 (m, 2H), 0.96 (t, J=7.2 Hz, 3H); $^{13}$C NMR (75.4 MHz, CDCl$_3$) δ 176.74, 164.12, 131.70, 130.23, 113.57, 95.69, 79.50, 55.38, 29.76, 21.91, 18.71, 13.35; IR (neat) 2958, 2934, 2872, 2238, 2199, 1635, 1594, 1573, 1508, 1460, 1421, 1316, 1251, 1164, 1113, 1026 cm$^{-1}$; MS (EI) m/z 216 (M$^+$, 63.27), 135 (100).

Example 16

Preparation of undec-6-yn-5-one

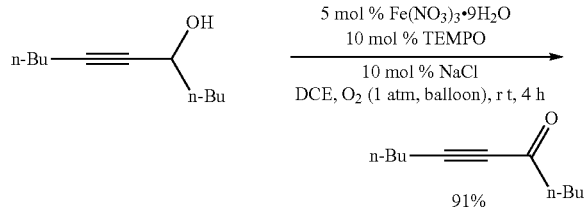

Example 16 was conducted in the same manner as example 1 except that the raw material was undec-6-yn-5-ol (168.4 mg, 1.0 mmol) and the reaction continues for 4 hours. The resulting product was undec-6-yn-5-one (151.8 mg, 91%). $^1$H NMR (300 MHz, CDCl$_3$) δ 2.52 (t, J=7.4 Hz, 2H), 2.37 (t, J=6.9 Hz, 2H), 1.71-1.60 (m, 4H), 1.60-1.28 (m, 4H), 0.97-0.89 (m, 6H); $^{13}$C NMR (75.4 MHz, CDCl$_3$) δ 188.43, 94.10, 80.87, 45.20, 29.71, 26.19, 22.08, 21.89, 18.57, 13.72, 13.40; IR (neat) 2959, 2933, 2873, 2213, 1672, 1465, 1243, 1168 cm$^{-1}$; MS (EI) m/z 165 (M$^+$-H, 0.07), 151 (M$^+$-CH$_3$, 4.57), 109 (M$^+$-Bu-n, 100).

Example 17

Preparation of dodec-1-yn-3-one

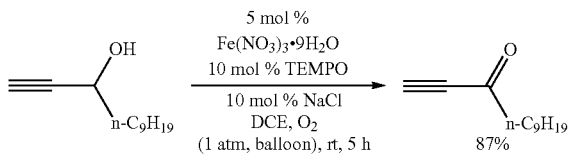

Example 17 was conducted in the same manner as example 1 except that the raw material was dodec-1-yn-3-ol (182.2 mg, 1.0 mmol) and the reaction continues for 5 hours. The resulting product was dodec-1-yn-3-one (156.5 mg, 87%). $^1$H NMR (300 MHz, CDCl$_3$) δ 3.20 (s, 1H), 2.58 (t, J=7.4 Hz, 2H), 1.75-1.60 (m, 2H), 1.37-1.20 (m, 12H), 0.88 (t, J=6.3 Hz, 3H); $^{13}$C NMR (75.4 MHz, CDCl$_3$) δ 187.51, 81.49, 78.18, 45.44, 31.82, 29.33, 29.26, 29.20, 28.87, 23.77, 22.63, 14.04; IR (neat): 2925, 2855, 2093, 1681, 1465, 1404, 1377, 1205, 1132, 1089, 1051 cm$^{-1}$; MS (EI) m/z 180 (M$^+$, 0.22), 179 (M$^+$-H, 0.85), 53 (100).

Example 18

Preparation of trans-3,7-dimethyl-2,6-octadienal

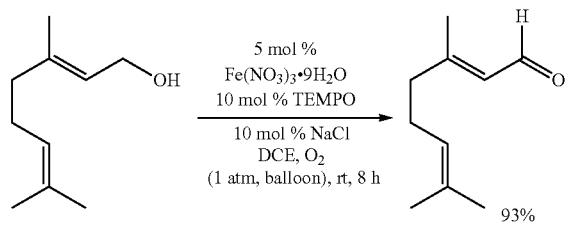

Example 18 was conducted in the same manner as example 1 except that the raw material was trans-3,7-dimethyl-2,6-octadienol (154.7 mg, 1.0 mmol) and the reaction continues for 8 hours. The resulting product was trans-3,7-dimethyl-2,6-octadienal (141.3 mg, 93%). $^1$H NMR (300 MHz, CDCl$_3$) δ 9.98 (d, J=7.5 Hz, 1H), 5.87 (d, J=7.2 Hz, 1H), 5.07 (s, 1H), 2.30-2.10 (m, 7H), 1.68 (s, 3H), 1.61 (s, 3H); $^{13}$C NMR (75.4 MHz, CDCl$_3$) δ 191.18, 163.70, 132.82, 127.34, 122.52, 40.52, 25.67, 25.54, 17.60, 17.47; IR (neat) 2968, 2917, 2856, 1671, 1632, 1611, 1442, 1379, 1193, 1120, 1044 cm$^{-1}$; MS (EI) m/z (%) 152 (M$^+$, 2.55), 69 (100).

Example 19

Preparation of trans-4-methyl-1-phenypent-1-en-3-one

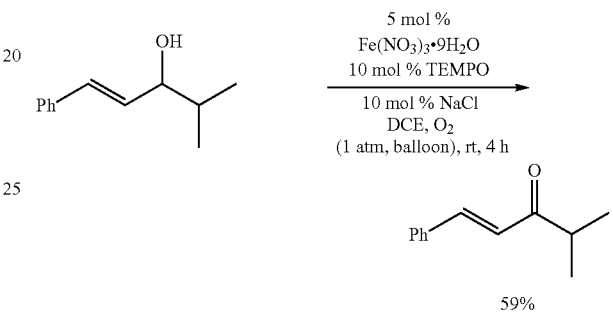

Example 19 was conducted in the same manner as example 1 except that the raw material was trans-4-methyl-1-phenypent-1-en-3-ol (176.6 mg, 1.0 mmol) and the reaction continues for 4 hours. The resulting product was trans-4-methyl-1-phenypent-1-en-3-one (102.8 mg, 59%). $^1$H NMR (300 MHz, CDCl$_3$) δ 7.61 (d, J=16.2 Hz, 1H), 7.57-7.52 (m, 2H), 7.41-7.34 (m, 3H), 6.82 (d, J=7.8 Hz, 1H), 2.93 (hept, J=6.9 Hz, 1H), 1.19 (s, 3H), 1.17 (s, 3H); $^{13}$C NMR (75.4 MHz, CDCl$_3$) δ 203.62, 142.27, 134.59, 130.21, 128.79, 128.16, 124.36, 39.14, 18.37; IR (neat) 3028, 1687, 1662, 1610, 1576, 1495, 1465, 1449, 1383, 1348, 1301, 1201, 1147, 1120, 1087, 1054 cm$^{-1}$; MS (EI) m/z 159 (M$^+$-CH$_3$, 7.13), 41 (100).

Example 20

Preparation of 2-phenylcyclohex-2-enone

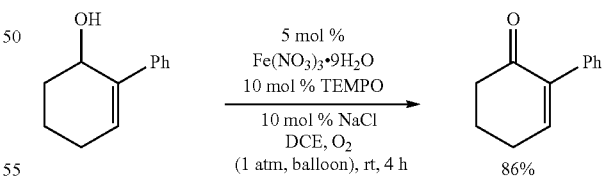

Example 20 was conducted in the same manner as example 1 except that the raw material was 2-phenylcyclohex-2-enol (175.0 mg, 1.0 mmol) and the reaction continues for 4 hours. The resulting product was 2-phenylcyclohex-2-enone (149.2 mg, 86%). $^1$H NMR (300 MHz, CDCl$_3$) δ 7.34-7.20 (m, 5H), 6.95 (t, J=4.1 Hz, 1H), 2.56-2.40 (m, 4H), 2.08-1.96 (m, 2H); $^{13}$C NMR (75.4 MHz, CDCl$_3$) δ 197.47, 147.75, 139.92, 136.32, 128.31, 127.61, 127.16, 38.73, 26.22, 22.57; IR (neat) 2948, 2930, 1661, 1553, 1491, 1443, 1427, 1357, 1315, 1279, 1261, 1208, 1155, 1119, 1071, 1032 cm$^{-1}$; MS (EI) m/z 172 (M$^+$, 59.46), 115 (100).

Example 21

Preparation of p-chlorobenzaldehyde

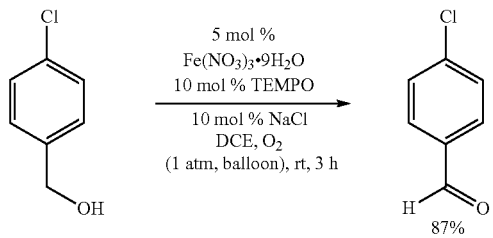 [SMILES: OCc1ccc(Cl)cc1 ; O=Cc1ccc(Cl)cc1]

Example 21 was conducted in the same manner as example 1 except that the raw material was p-chlorobenzyl alcohol (142.3 mg, 1.0 mmol) and the reaction continues for 3 hours. The resulting product was p-chlorobenzaldehyde (122.2 mg, 87%). $^1$H NMR (300 MHz, CDCl$_3$) δ 9.98 (s, 1H), 7.82 (d, J=7.5 Hz, 2H), 7.51 (d, J=7.8 Hz, 2H); $^{13}$C NMR (75.4 MHz, CDCl$_3$) δ 190.75, 140.91, 134.72, 130.85, 129.42; IR (neat): 2856, 1699, 1588, 1575, 1485, 1385, 1295, 1264, 1205, 1165, 1092, 1012 cm$^{-1}$; MS (EI) m/z 142 (M$^+$($^{37}$Cl), 10.04), 140 (M$^+$($^{35}$Cl), 35.62), 41 (100).

Example 22

Preparation of p-methoxybenzaldehyde

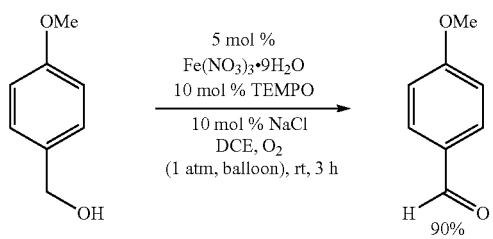 [SMILES: COc1ccc(CO)cc1 ; COc1ccc(C=O)cc1]

Example 19 was conducted in the same manner as example 1 except that the raw material was p-methoxybenzyl alcohol (137.8 mg, 1.0 mmol) and the reaction continues for 3 hours. The resulting product was p-methoxybenzaldehyde (122.4 mg, 90%). $^1$H NMR (300 MHz, CDCl$_3$) δ 9.87 (s, 1H), 7.82 (d, J=8.4 Hz, 2H), 6.99 (d, J=8.4 Hz, 2H), 3.87 (s, 3H); $^{13}$C NMR (75.4 MHz, CDCl$_3$) δ 190.24, 164.13, 131.45, 129.49, 113.84, 55.09; IR (neat) 2840, 2739, 1680, 1595, 1576, 1510, 1460, 1426, 1393, 1314, 1255, 1214, 1182, 1157, 1108, 1021 cm$^{-1}$; MS (EI) m/z 136 (M$^+$, 69.21), 135 (100).

Example 23

Preparation of p-nitrobenzaldehyde

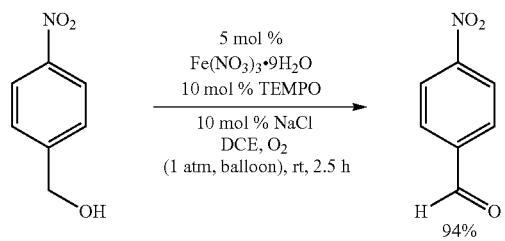 [SMILES: O=[N+]([O-])c1ccc(CO)cc1 ; O=Cc1ccc([N+](=O)[O-])cc1]

Example 23 was conducted in the same manner as example 1 except that the raw material was p-nitrobenzyl alcohol (153.1 mg, 1.0 mmol) and the reaction continues for 2.5 hours. The resulting product was p-nitrobenzaldehyde (141.6 mg, 94%). $^1$H NMR (300 MHz, CDCl$_3$) δ 10.16 (s, 1H), 8.39 (d, J=8.4 Hz, 2H), 8.07 (d, J=8.4 Hz, 2H); $^{13}$C NMR (75.4 MHz, CDCl$_3$) δ 190.23, 140.07, 130.45, 124.28; IR (neat) 2852, 1707, 1606, 1539, 1382, 1346, 1325, 1287, 1198, 1105, 1008 cm$^{-1}$; MS (EI) m/z 151 (M$^+$, 73.95), 51 (100).

Example 24

Preparation of Acetophenone

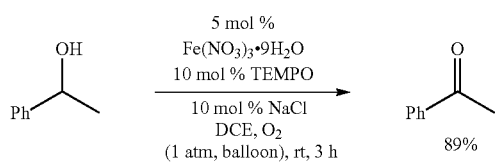

Example 24 was conducted in the same manner as example 1 except that the raw material was 1-phenyl ethanol (121.4 mg, 1.0 mmol) and the reaction continues for 3 hours. The resulting product was acetophenone (106.9 mg, 89%). $^1$H NMR (300 MHz, CDCl$_3$) δ 7.96 (d, J=7.8 Hz, 2H), 7.56 (t, J=7.4 Hz, 1H), 7.46 (t, J=7.7 Hz, 2H), 2.60 (s, 3H); $^{13}$C NMR (75.4 MHz, CDCl$_3$) 198.09, 137.15, 133.05, 128.54, 128.27, 26.53; IR (neat) 1681, 1598, 1582, 1448, 1358, 1263, 1180, 1078, 1024 cm$^{-1}$; MS (EI) m/z 120 (M$^+$, 33.35), 77 (100).

Example 25

Preparation of Hexadecanal

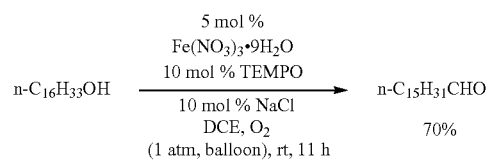

Example 25 was conducted in the same manner as example 1 except that the raw material was hexadecanol (242.7 mg, 1.0 mmol) and the reaction continues for 11 hours. The resulting product was hexadecanal (168.5 mg, 70%). $^1$H NMR (300 MHz, CDCl$_3$) δ 9.76 (s, 1H), 2.41 (t, J=7.4 Hz, 2H), 1.68-1.56 (m, 2H), 1.36-1.18 (m, 24H), 0.88 (t, J=6.2 Hz, 3H); $^{13}$C NMR (75.4 MHz, CDCl$_3$) δ 202.82, 43.89, 31.91, 29.64, 29.56, 29.40, 29.33, 29.16, 22.66, 22.08, 14.06; IR (neat) 2912, 2849, 1729, 1704, 1470, 1411, 1392, 1373 cm$^{-1}$; MS (EI) m/z 240 (M$^+$, 2.20), 57 (100).

Example 26

Preparation of tridecan-2-one

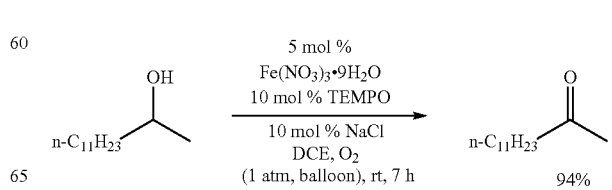

Example 23 was conducted in the same manner as example 1 except that the raw material was tridecan-2-ol (201.1 mg, 1.0 mmol) and the reaction continues for 7 hours. The resulting product was tridecan-2-one (186.4 mg, 94%). $^1$H NMR (300 MHz, CDCl$_3$) δ 2.31 (t, J=7.4 Hz, 2H), 2.02 (s, 3H), 1.53-1.42 (m, 2H), 1.27-1.10 (m, 16H), 0.78 (t, J=6.3 Hz, 3H); $^{13}$C NMR (75.4 MHz, CDCl$_3$) δ 208.60, 43.52, 31.71, 29.47, 29.42, 29.29, 29.22, 29.14, 28.99, 23.66, 22.47, 13.84; IR (neat) 2923, 2853, 1717, 1465, 1411, 1358, 1260, 1226, 1162 cm$^{-1}$; MS (EI) m/z 198 (M$^+$, 2.18), 43 (100).

Example 27

Preparation of Cyclohexanone

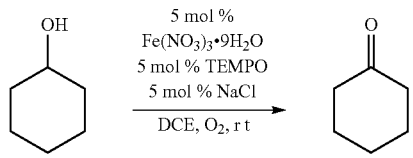 [SMILES: OC1CCCCC1 ; O=C1CCCCC1]

Fe(NO$_3$)$_3$.9H$_2$O (2.0681 g, 5.0 mmol), TEMPO (781.3 mg, 5.0 mmol), NaCl (299.0 mg, 5.0 mmol), and DCE (50 mL) were added to a 100 mL-three-necked flask, and were stirred for 5 mins at room temperature under oxygen atmosphere. Cyclohexanol (10.0718 g, 100.0 mmol) was then added dropwise to the reaction solution. The reaction was exothermic, and the reaction temperature was kept below 50° C. The reaction was monitored by TLC till it was complete. The resulting mixture was purified by distillation under reduced pressure (20 mmHg, 68-71° C.) to afford the product cyclohexanone (8.33 g, 85%). $^1$H NMR (300 MHz, CDCl$_3$) δ 2.33 (t, J=6.6 Hz, 4H), 1.90-1.80 (m, 4H), 1.77-1.63 (m, 2H); $^{13}$C NMR (75.4 MHz, CDCl$_3$) δ 212.13, 41.64, 26.73, 25.22.

Example 28

Preparation of Acetophenone

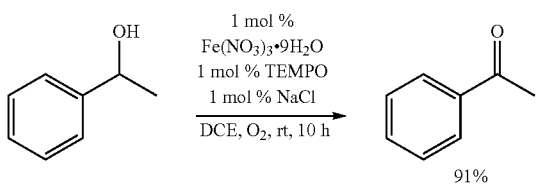

Fe(NO$_3$)$_3$.9H$_2$O (16.1607 g, 40.0 mmol), TEMPO (6.2510 g, 40.0 mmol), NaCl (2.3377 g, 40.0 mmol) and DCE (400 mL) were added to a 2 L-three-necked flask, and were stirred for 10 mins at room temperature under oxygen atmosphere. 1-Phenyl ethanol (488.64 g, 4.0 mol) was then added dropwise to the reaction solution. The reaction was exothermic, and the reaction temperature was kept below 50° C. The reaction was monitored by TLC till it was complete. The reaction solvent DCE was recovered after distillation under atmospheric pressure (350 mL, recovery of 88%) and acetophenone was obtained after further distillation under reduced pressure (b.p. 98~100° C./20 mmHg, 436.6414 g, 91%).

Examples 29-34

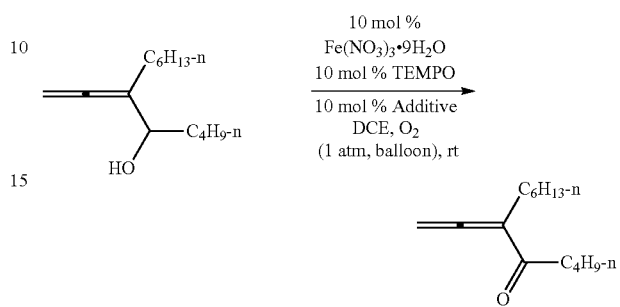

Fe(NO$_3$)$_3$.9H$_2$O (0.05 mmol), 1,2-dichloroethane (DCE, 4 mL), TEMPO (0.05 mmol) and additive (0.05 mmol) were added to a 10 mL-three-necked flask and were stirred for 5 mins at room temperature under oxygen atmosphere. 3-Hexylocta-1,2-dien-4-ol (0.5 mmol) was dissolved in DCE (1 mL) and then was added dropwise to the reaction solution. The reaction was monitored by TLC till it was complete. The resulting reaction solution was diluted with ether (30 mL), dried over anhydrous MgSO$_4$, filtered by a short pad of silica gel and condentrated under reduced pressure, and then trimethylbenzene (46 uL) was added, and conversion and yield were analyzed by nuclear magnetic resonance spectra ($^1$H NMR, 300 MHz).

| Example | Additive | Reaction time (h) | Conversion (%, NMR) | Yield (%, NMR) |
| --- | --- | --- | --- | --- |
| 29 | Nil | 48 | 75 | 43 |
| 30 | LiCl•H$_2$O | 10 | 95 | 74 |
| 31 | NaCl | 4 | 100 | 72 |
| 32 | KCl | 4.5 | 100 | 81 |
| 33 | RbCl | 3 | 100 | 74 |
| 34 | CsCl | 3 | 100 | 73 |

The invention claimed is:

1. A process for producing aldehydes or ketones by aerobic oxidation of alcohol comprising a step of oxidizing alcohol to aldehyde or ketone at room temperature, under neutral conditions, and in an organic solvent for about 1 to 24 hours using oxygen or air as oxidant, and ferric nitrate, 2,2,6,6-tetramethylpiperidinyloxy and one or more inorganic chloride as catalysts, wherein a molar ratio of said alcohol to said 2,2,6,6-tetramethylpiperidinyloxy, to said ferric nitrate, and to said one or more inorganic chloride is 100:1~10:1~10:1~10, wherein said one or more inorganic chloride is selected from the group consisting of sodium chloride, potassium chloride, lithium chloride, rubidium chloride and cesium chloride.

2. The process for producing aldehydes or ketones by aerobic oxidation of alcohol of claim 1, wherein said alcohol is R$_1$R$_2$CHOH or C5-C8 cyclic alcohols,
    wherein, R$_1$ represents hydrogen; C1-16 alkyl; an alkenyl substituted with groups R$_3$ and/or R$_4$; allenyl substituted with groups R$_5$ and/or R$_6$; alkynyl, aryl, trifluoromethylphenyl, nitrophenyl, halophenyl or C1-C4 alkoxyphenyl substituted with $R_7$; and $R_2$ represents hydrogen, C1-16 alkyl, aryl, trifluoromethylphenyl, halophenyl or methoxyphenyl, and wherein, $R_3$ represents C1-C16 alkyl or aryl; $R_4$ represents hydrogen, C1-C6 alkyl or aryl; $R_5$ represents hydrogen, C1-C9 alkyl, arylphenyl or benzyl; $R_6$ represents hydrogen, C4-C9 alkyl, aryl or benzyl; and R7 represents hydrogen, C1-C12 alkyl, trimethylsilyl, aryl, halophenyl, nitrophenyl or methoxyphenyl.

3. The process for producing aldehydes or ketones by aerobic oxidation of alcohol of claim 2, wherein said aryl is phenyl, halophenyl, alkoxyphenyl or naphthyl.

4. The process for producing aldehydes or ketones by aerobic oxidation of alcohol of claim 1, said C5-C8 cyclic alcohols is cyclopentanol, cyclohexanol, cycloheptanol or cyclooctanol.

5. The process for producing aldehydes or ketones by aerobic oxidation of alcohol of claim 1, wherein said organic solvent is benzene, toluene, dichloromethane, 1,2-dichloroethane, 1,1-dichloroethane, 1,2-dichloropropane, 1,3-dichloropropane, nitromethane, ethylene glycol dimethyl ether, tetrahydrofuran, acetonitrile, ethyl acetate or any combinations thereof.

6. The process for producing aldehydes or ketones by aerobic oxidation of alcohol of claim 1, wherein the inorganic chloride is sodium chloride.

* * * * *